United States Patent [19]

Brown et al.

[11] 3,969,466
[45] July 13, 1976

[54] PREPARATION OF HYDRAZODICARBONAMIDE

[75] Inventors: Robert W. Brown, Middlebury; Byron A. Hunter, Woodbridge; Franklin H. Barrows, Beacon Falls, all of Conn.

[73] Assignee: Uniroyal Inc., New York, N.Y.

[22] Filed: Sept. 9, 1974

[21] Appl. No.: 504,015

[52] U.S. Cl. ............................................. 260/554
[51] Int. Cl.[2] ....................................... C07C 133/02
[58] Field of Search ..................................... 260/554

[56] References Cited
UNITED STATES PATENTS

| | | | |
|---|---|---|---|
| 2,692,281 | 10/1954 | Newby et al. | 260/554 |
| 3,153,089 | 10/1964 | Ameen | 260/554 X |

FOREIGN PATENTS OR APPLICATIONS

| | | | |
|---|---|---|---|
| 2,228,833 | 1/1973 | Germany | |
| 66069S | 11/1969 | Japan | 260/554 |
| 67837R | 11/1967 | Japan | 260/554 |

*Primary Examiner*—Daniel E. Wyman
*Assistant Examiner*—Thomas A. Waltz
*Attorney, Agent, or Firm*—Bruce F. Jacobs

[57] ABSTRACT

A process for preparing hydrazodicarbonamide directly from a ketazine and urea in water without any acid catalyst according to the following reaction is disclosed.

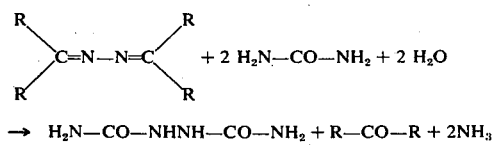

$\rightarrow$ H$_2$N—CO—NHNH—CO—NH$_2$ + R—CO—R + 2NH$_3$ wherein the R groups may be the same or different.

5 Claims, No Drawings

PREPARATION OF HYDRAZODICARBONAMIDE

BACKGROUND OF THE INVENTION

1. Field of the Invention

This invention relates to a novel process for preparing hydrazodicarbonamide directly from ketazines and urea in water without an acid catalyst. The reaction is as follows:

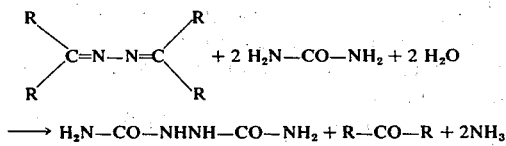

$$\longrightarrow H_2N-CO-NHNH-CO-NH_2 + R-CO-R + 2NH_3$$

where the R's are the same or different and are alkyl groups containing up to 8 carbon atoms or are joined together to form aliphatic rings of 5–6 carbon atoms.

2. Description of the Prior Art

While a variety of art-known processes for preparing hydrazodicarbonamide are presently being used, there are still extant problems in the production of the hydrazodicarbonamide, particularly dealing with increasing the yields of the reaction.

Particularly, German Offenlegungschrift No. 2,228,833 discloses the preparation of hydrazodicarbonamide in modest yield (52–72% of theoretical) by heating a ketazine with an aqueous solution of urea and sulfuric acid as a catalyst.

SUMMARY OF THE INVENTION

In contrast to the above reference, this invention enables the production of hydrazodicarbonamide in greatly improved yields without the sulfuric acid merely by heating an aqueous solution of a ketazine with excess urea. The removal of the acid not only increases yields, but also makes the process more economical and avoids the build-up of salts in the aqueous liquors.

DESCRIPTION OF THE PREFERRED EMBODIMENTS

Ketazines suitable for this invention are of the formula

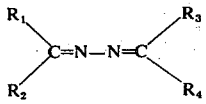

where $R_1$, $R_2$, $R_3$ and $R_4$ are alkyl groups containing up to 8 carbon atoms each or either ($R_1$ and $R_2$) or ($R_3$ and $R_4$) together may constitute an aliphatic ring of 5 to 6 carbon atoms. The R groups may be the same or different. In the preferred ketazines, $R_1$ and $R_3$ will be the same and $R_2$ and $R_4$ will be the same, such structures being descriptively derived from the reaction of two moles of a single ketone with hydrazine. Thus the ketazine may be descriptively derived from acetone, methyl ethyl ketone, diethyl ketone, butanone-2, methyl isopropyl ketone, methyl isobutyl ketone, dibutyl ketone, diisobutyl ketone, pentanone-2, diamyl ketone, dihexyl ketone, dihpeptyl ketone, dioctyl ketone, cyclohexanone, cyclopentanone and other ketones containing up to 17 carbon atoms, or from mixtures of such ketones.

Procedures for preparing the ketazines from ammonia and chlorine (or from ammonia and hypochlorite) in the presence of ketones is well known from such as U.S. Pat. Nos. 2,993,758; 3,077,383; 3,415,882 and 3,728,390 incorporated herein by reference.

The process of this invention is to heat an aqueous solution of excess urea and a ketazine. The molar ratio of urea to the ketazine must be at least 2 to 1 and may be as high as 20/1 or even higher if so desired, though usually this ratio is conveniently kept within a range of 3/1 to 10/1, preferably 4/1 to 8/1. The heating is carried out above about 50° up to 150°C. or even higher depending upon the actual ketazine employed. Preferably the temperature is 90°–130°C. and most preferably 100°–120°C. The reaction time is generally for one-half to 48 hours or longer, but usually 4 to 24 hours, and in most cases for 5 to 12 hours.

In order to increase the economy and efficiency of the process it is advantageous to recycle the urea solution which is used in excess. By repeatedly passing the evolved vapors (and ammonia) of the reaction through a fractionating column which permits the slow distillation of the regenerated ketone and water and the return of any unhydrolyzed ketazine to the reaction vessel (selective distillation) the recycling may be accomplished. The recovered ketone in the condensed distillate (as well as the ammonia) can be reused to form more ketazine.

The compounds of this process are useful as intermediates for the preparation of azodicarbonamide, a commercial blowing agent used in the manufacture of cellular polymers.

The following examples are intended to be merely illustrative of the invention and not in limitation thereof.

EXAMPLE 1

Reaction of Methyl Ethyl Ketazine With Aqueous Urea a. First cycle 360g (6.0 moles) of urea and 240 cc water to make a 60% urea solution) are mixed with 140g (1.0 mole) of methyl ethyl ketazine in a 2-liter two-neck flask. A stirrer, heating mantle, thermometer and an eleven inch distillation column (packed with glass helices) attached to the condenser and receiver are added to the set-up. A gas outlet tube is attached to the receiver to allow the ammonia produced by the reaction to be vented to an acid trap.

The stirred solution is heated to reflux temperature (pot temperature 103°C.). Ammonia gas is evolved and an azeotrope of methyl ethyl ketone and water is collected in the receiver. Refluxing is continued for 1.5 hours when a crystalline precipitate begins to form. The refluxing is continued for an additional 5.5 hours (total reflux time — 7 hours). Distillation of methyl ethyl ketone has ceased at this point. The reaction mixture is cooled to 80°C. and the crystalline product is filtered off and washed with 200 ml. water. This portion of the filtrate is saved for the next batch. (See (b) below). The solid product is further washed with one liter of water and the washings discarded. The solid is dried at 60°C. Yield is 100g. The recovered methyl ethyl ketone weighs 131g.

b. Second Cycle

The filtrate and first 200cc of washings from part (a) above are charged back into the reaction flask. Water is removed by distillation until the pot temperature reaches 100°C. (125cc water removed). Then 120g of urea (2.0 moles) and 140g methyl ethyl ketazine (1.0 mole) are added to the concentrated urea solution. As in part (a), the reaction mixture is allowed to reflux for 7 hours, with the pot temperature reaching 112°C. At this point the reaction mixture is cooled to 80°C. and the white solid filtered off and washed with 200 ml. water. The filtrate and the 200 ml. washings are reserved for use in cycle (3). The precipitate is further washed with a liter of water and these washings are discarded. The solid is dried at 60°C. Yield is 118g. Recovered also is 133g. methyl ethyl ketone.

c. Third-Sixth Cycles

The process is then repeated until a total of six cycles are conducted in accordance with the above procedures.

The yields of hydrazodicarbonamide and the amounts of recovered methyl ethyl ketone are shown in Table I.

TABLE I

SUMMARY OF EXAMPLE I
Yield (g)

| Cycle | Hydrazodi-carbonamide | Ketone Recovered (g) |
|---|---|---|
| (1) | 100 | 131 |
| (2) | 118 | 133 |
| (3) | 111 | 129 |
| (4) | 96 | 122 |
| (5) | 124 | 128 |
| (6) | 101 | 126 |
| Total Yield | 650g | 769g |

Theory=118×6=708g        Theory=144×6=864g
650/708=91.8%              769/864=89%

EXAMPLE II

Preparation of Hydrazodicarbonamide from Diethyl Ketazine

Cycle (1)

In an apparatus similar to that described in Example I, part A, a mixture of 360g (6.0 moles) urea, 240 ml. water and 168g (1.0 mole) diethyl ketazine is stirred and heated to reflux for a period of 6 hours. Ammonia gas is evolved and an azeotrope of diethyl ketone and water is collected in the receiver. The crystalline hydrazodicarbonamide is filtered off and washed with 200 ml. water. The filtrate and 200 ml. washings are saved for cycle (2) (see below). The solid product is washed with additional water (which is discarded) and dried. Yield is 107.5g (91.1%) and 164g of diethyl ketone is recovered (95.4%).

Cycle (2)

Following the procedure previously described in Example I, Cycle 2, the filtrate and washings from cycle (1) are concentrated by removal (distillation) of 125 ml. water. To the residue in the 2 liter flask is added 120 g urea and 168g of diethyl ketazine. The mixture is refluxed for six hours as the azeotrope of diethyl ketone and water is slowly distilled off, along with the evolution of ammonia gas. The crystalline product, after washing and drying weighs 114g (96.6%), while the recovered diethyl ketone weights 163g (95%).

EXAMPLE III

Preparation of Hydrazodicarbonamide from Dimethyl Ketazine

Cycle (1)

Using the apparatus and general procedure of Example II, a mixture of 360g (6.0 moles) urea, 240 ml. water and 112g (1.0 mole) dimethyl ketazine is heated for 8 hours with gradual removal of acetone and water. The crystalline hydrazodicarbonamide is filtered off and washed with 200 ml. of water. The filtrate and 200 ml. washings are reserved for cycle (2). The solid is washed with additional water and dried. Yield is 93g (78.8%) recovered 92g (79.3%) of acetone.

Cycle (2)

The filtrate and 200 ml. washings from cycle (1), above are concentrated by distillation of 125 ml. water. To the residual urea solution is added 120g (2.0 moles) urea and 112g (1.0 mole) dimethyl ketazine. The product is heated to boiling for 8 hours with the slow removal of ammonia, acetone and water. The crystalline product is filtered, washed and dried. Yield is 101g (85.6%) and the recovered acetone weighs 98g (84.5%).

EXAMPLE IV

Preparation of Hydrazodicarbonamide from Methyl Isobutyl Ketazine

The apparatus and procedure previously described are employed in reacting a mixture of 360g (6.0 moles) urea, 240 ml. water and 196g (1.0 mole) methyl isobutyl ketazine. The mix is stirred and heated to reflux temperature for 25 hours with slow removal of methyl isobutyl ketone. The reaction is much slower than the previous preparations. There is recovered 57g (49.1%) of hydrazodicarbonamide and 116g (58%) of methyl isobutyl ketone. A good portion (79g or 40.3%) of methyl isobutyl ketazine is recovered from the filtrate.

EXAMPLE V

Preparation of Hydrazodicarbonamide from Cyclohexylketazine

In a manner similar to Example IV, 360g urea, 240 ml. water and 192g cyclohexyl ketazine are stirred and heated for 12 hours. Cyclohexanone slowly is distilled. Hydrazodicarbonamide begins separating after the first 3 hours of heating. 100 ml. of water are added after 6 hours to replace that carried over in the azeotrope. Another 100 ml. water are added after 10 hours. The final temperature is 120°C. The mixture is cooled to 80°C. and the solid product filtered off, washed and dried. Yield is 100g (84.7%) hydrazodicarbonamide, mp=257°C. (dec). 178g of cyclohexanone is also recovered (90%).

EXAMPLE VI

Preparation of Hydrazodicarbonamide from Cyclopentaketazine

In the manner described above 360g urea, 240 ml. water and 160.7g (0.98 mole), of cyclopentaketazine are stirred and heated to reflux temperature (109°C.) and boiled with slow distillation of cyclopentanone for a period of 7 hours. Hydrazodicarbonamide appears after 2 hours. The final reflux temperature is 112°C. The mix is then cooled to 80°C. and the hydrazodicarbonamide filtered off, washed with water and dried. Yield is 88g (76.1%). This melts with decomposition at 249°C. Also recovered is 129g (74.7%) of cyclopentanone.

What is claimed is:

1. A process for producing hydrazodicarbonamide by heating urea and water, and a ketazine of the formula

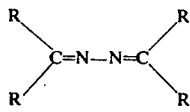

wherein the R groups are the same or different and are alkyl groups containing up to 8 carbon atoms or are joined together to form aliphatic rings of 5–6 carbon atoms, to a temperature of about 90° to 130°C. in the absence of an acid catalyst. wherein the urea is present in at least two moles per mole of ketazine.

2. The process of claim 1 wherein the ketazine is selected from the group consisting of dimethyl ketazine, methyl ethyl ketazine, diethyl ketazine, cyclopentyl ketazine and cyclohexyl ketazine.

3. The process of claim 1 wherein the urea is present in 3 to 10 moles per mole of ketazine.

4. The process of claim 1 wherein the urea is present in 4 to 8 moles per mole of ketazine.

5. The process of claim 1 wherein the heating continues for one-half to 48 hours.

* * * * *